United States Patent [19]

Yamamoto et al.

[11] 4,256,591

[45] Mar. 17, 1981

[54] LUBRICANT, LUBRICANT COMPOSITION AND METHOD FOR LUBRICATING A SURFACE

[75] Inventors: Satoshi Yamamoto; Toshiyuki Hirae, both of Ibaragi; Yasunori Koizumi, Yokkaichi, all of Japan

[73] Assignees: Mitsubishi Petrochemical Co., Ltd.; Yukamelamin Company, Limited, both of Tokyo, Japan

[21] Appl. No.: 69,404

[22] Filed: Aug. 24, 1979

[30] Foreign Application Priority Data

Aug. 24, 1978 [JP] Japan ................ 53-103229

[51] Int. Cl.³ ............... C10M 1/20; C10M 1/32; C10M 7/16; C10M 7/30
[52] U.S. Cl. .................. 252/12; 252/49.3; 252/49.5; 252/50; 252/51.5 R; 544/192
[58] Field of Search .............. 252/12, 49.3, 49.5, 252/50, 51.5 R; 544/192

[56] References Cited

U.S. PATENT DOCUMENTS 3,278,436  10/1966  Dazzi et al. ............. 252/51.5 R
3,532,635  10/1970  Hans ..................... 252/551 X

*Primary Examiner*—W. J. Shine
*Attorney, Agent, or Firm*—Sughrue, Rothwell, Mion, Zinn and Macpeak

[57] ABSTRACT

A lubricant containing an adduct of melamine and isocyanuric acid or cyanuric acid is effective for use in high-temperature, low-temperature, or high-pressure atmospheres, or places where black-color producing contamination is not desired, or in metal working, cutting or grinding of metals. The adduct not only functions as a solid lubricant but also as an agent to thicken liquid lubricants such as mineral oil, and it is used as a powder, or as suspended in a lube oil, grease or water, or it can be applied to surfaces subject to wear using a synthetic resin such as vinyl resin or epoxy resin as a binder.

44 Claims, 1 Drawing Figure

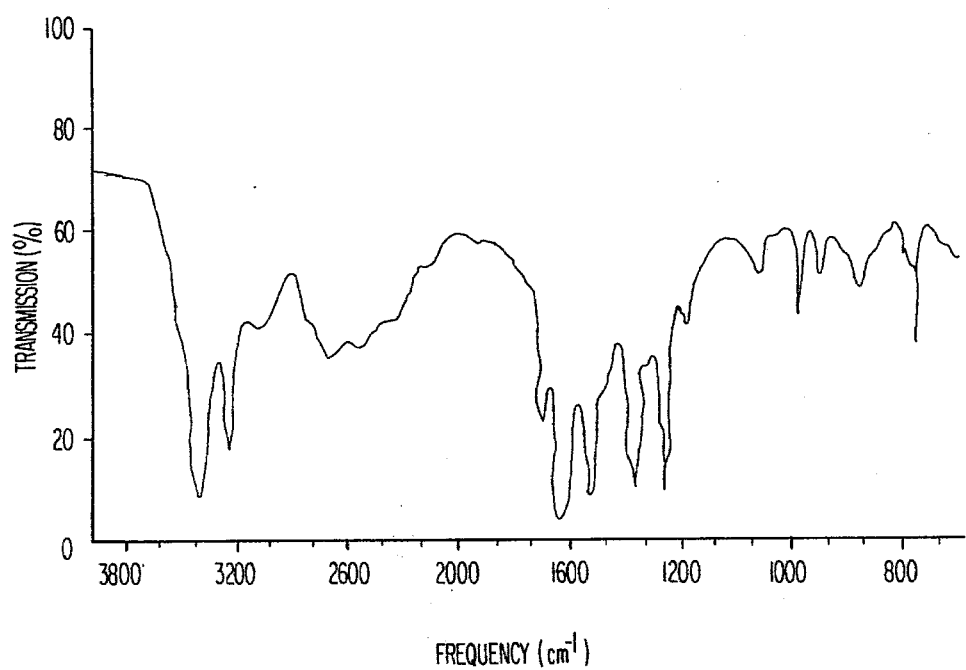

LUBRICANT, LUBRICANT COMPOSITION AND METHOD FOR LUBRICATING A SURFACE

BACKGROUND OF THE INVENTION

1. Field of the Invention

This invention relates to a lubricant comprising an adduct of melamine and isocyanuric acid or cyanuric acid. While solid lubricants commonly used in practice are inorganic compounds or organic polymers, the adduct of melamine and (iso)cyanuric acid according to this invention is characterized as an organic salt, and its lubricating performance has not been appreciated. The lubricant prepared according to this invention effectively prevents seizures or minimizes wear to a degree that has not been possible with conventional lube oils, in particular it is able to minimize wear under extremely high pressures to a higher degree than the conventional solid lubricants.

2. Description of the Prior Art

Lubricants are classified by form into solid lubricants, liquid lube oils and semisolid grease.

Solid lubricants are applied in high-temperature, low-temperature or high-pressure uses where lube oils cannot effectively be used, or in food processing machines in which the odor of lube oils is not tolerable. Conventional solid lubricants include molybdenum disulfide, tungsten disulfide, colloidal graphite, barium oxide and zinc oxide powder having crystalline structure, or sodium borate, lead oxide and zinc monoxide powder having noncrystalline structure, all of them are inorganic compounds. Examples of an organic solid lubricant are polymers such as polytetrafluoroethylene. Solid lubricants may be used per se but more often than not they are blended with oils into a paste form or incorporated in a lube oil or grease composed of a mineral oil blended with a metal soap.

Molybdenum disulfide and colloidal graphite which are common high-performance solid lubricants are not advantageous. They are expensive and when they are used independently as a solid lubricant, molybdenum disulfide is oxidized at high temperature to produce molybdenum oxide which is so abrasive that the resulting wear is more excessive than without lubrication. Furthermore, when mixed with lube oil or grease these solids provide a dark product with low commercial value and therefore limited utility is produced. Due to their high specific gravity, molybdenum disulfide and colloidal graphite cannot be stably dispersed in a solvent or water without specially sophisticated technology.

While a melamine/cyanuric acid adduct has been used as an opacifier in products such as liquid detergents, lotions, shampoos and the like, as disclosed in U.S. Pat. No. 3,532,635, its use as a lubricant has not been recognized.

SUMMARY OF THE INVENTION

It is therefore one object of this invention to provide an improved solid lubricant comprising an adduct of isocyanuric acid or cyanuric acid (the two will hereunder be collectively referred to as an (iso)cyanuric acid) and melamine (the adduct will hereunder be referred to as a melamine/(iso)cyanuric acid adduct) which is free from the above-mentioned defects of the conventional solid lubricants.

It is another object of this invention to provide a melamine/(iso)cyanuric acid adduct which can be incorporated in a conventional lube oil or grease to enhance its load carrying capacity.

It is a further object of this invention to provide an aqueous lubricant which exhibits high cooling effect, pressure resistance or wear resistance in a highly exothermic state or under extremely high pressures.

It is still another object of this invention to provide a lubricant comprising said adduct which is to be applied to wearing surfaces, with a vinyl resin or epoxy resin used as a binder.

BRIEF DESCRIPTION OF THE DRAWING

The FIGURE is a chart showing the IR spectrum of the melamine/(iso)cyanuric acid adduct of which the lubricant of this invention is composed.

DETAILED DESCRIPTION OF THE INVENTION

1. Melamine/(Iso)cyanuric Acid Adduct

The solid lubricant of this invention is prepared from melamine and cyanuric acid or isocyanuric acid by various methods identified in (a) and (b) (i) through (iii) below. A melamine/isocyanuric acid adduct produced by reacting equimolar amounts of melamine and isocyanuric acid has a sublimation temperature of about 440° C. as measured by differential thermal analysis, and can be clearly distinguished from melamine and isocyanuric acid which sublime at 350° C. and 390° C., respectively.

The adduct provides an infrared absorption spectrum which differs from that of melamine or (iso)cyanuric acid, as shown in accompanying FIGURE.

The adduct presumably has melamine and isocyanuric acid bonded together intermolecularly in the form of an organic salt. X-ray diffraction spectrometry reveals the high crystallinity of the adduct having acute peaks at $2\eta = 10.92$ degrees, 11.95 degrees and 28.15 degrees and so forth. The adduct as observed under an electron microscope has an acicular crystalline structure.

2. Preparation of the Adduct

The melamine/(iso)cyanuric acid adduct of this invention is prepared by any one of the following methods:

(a) Mixing an aqueous solution of melamine with an aqueous solution of (iso)cyanuric acid;

(b) Any one of the following methods (i) through (iii) wherein melamine is reacted with (iso)cyanuric acid as either one or both are dispersed in a solid state in an aqueous medium (reference can be made to Japanese Patent Application No. 30998/78);

(ia) Adding solid (iso)cyanuric acid to an aqueous solution or dispersion of melamine, or vice versa in the order of addition;

(ib) Adding solid melamine to an aqueous solution or dispersion of (iso)cyanuric acid, or vice versa in the order of addition;

(iia) Adding an aqueous solution of (iso)cyanuric acid to an aqueous dispersion of melamine, or vice versa in the order of addition;

(iib) Adding an aqueous solution of melamine to an aqueous dispersion of (iso)cyanuric acid, or vice versa in the order of addition;

(iii) Stirring a mixture of aqueous liquid, solid (iso)cyanuric acid and solid melamine each added in an amount of exceeding its respective solubility.

Generally, the preparative procedure is to react melamine and (iso)cyanuric acid in an aqueous medium at temperatures ranging from room temperature to 200° C., preferably from 50° C. to 100° C., and at a pressure ranging from 1 to 15 atms, preferably at atmospheric pressure. The reaction time adopted ranges from about 10 minutes to 10 hours, preferably 10 minutes to 1 hour. To accelerate the reaction the pH of the medium during the reaction may be maintained at alkali side (7.5–10) or at acidic side (2–6.5) by the aid of alkali such as caustic alkali, amine, ammonia or of acid such as mineral acid, organic acid, followed by neutralization at the end of the reaction.

In the reactions described above, melamine can be mixed with (iso)cyanuric acid in varying ratios, but an equimolar mixture will provide a melamine/(iso)cyanuric acid adduct of high purity. An excess of either melamine or (iso)cyanuric acid is not industrially advantageous for producing a high purity melamine/(iso)cyanuric acid adduct because the excess melamine or (iso)cyanuric acid must be separated from the resulting adduct. Therefore, the desired adduct is most preferably produced by preparing an equimolar mixture of melamine and (iso)cyanuric acid for reaction. If either melamine or (iso)cyanuric acid or both are added portionwise during reaction, it is important to control their molar ratio so that it is 1:1 at completion of the reaction.

Some applications of the lubricant may require a mixture of the melamine/(iso)cyanuric acid adduct and melamine or (iso)cyanuric acid. In such cases an excess amount of either melamine or (iso)cyanuric acid may be used so that the resulting adduct contains unreacted melamine or (iso)cyanuric acid.

Referring to the method (b), either melamine or (iso)cyanuric acid or both are dispersed as solids in an aqueous medium, this means that melamine or (iso)cyanuric acid or both are present in an aqueous medium in an amount exceeding their solubility in the medium at the reaction temperature. The preferred concentration of the dispersion is such that 100 parts by weight of the aqueous medium contains 6 to 100 parts by weight of the melamine and (iso)cyanuric acid combination. Use of more than 100 parts by weight of the melamine and (iso)cyanuric acid combination should be avoided because of the difficulties which may result in mixing under stirring.

Dispersing melamine or (iso)cyanuric acid in water may be facilitated by adding 0.01 to 10 parts by weight of a surfactant or dispersing agent which will be described hereinafter to 100 parts by weight of the solid reactant(s).

In the reaction method described above, the melamine/(iso)cyanuric acid adduct, which is substantially insoluble in the aqueous medium in the pH range from 6.5–7.5, is obtained as a precipitate having a particle size of 0.1 to several microns by adjusting the pH to this range.

3. Applications of Lubricant (a) Solid lubricant

The melamine/(iso)cyanuric acid adduct prepared according to this invention can be used as a solid lubricant per se in the form of a fine powder. To be more specific, if a powder of the melamine/(iso)cyanuric acid adduct is applied to the contact surfaces of two cyclically moving solid objects and the one surface is caused to frictionally engage the other, the adduct will form a very smooth interface which reduces the coefficient of friction between the two surfaces to provide smooth motion between the solid objects.

The adduct can be formulated into various forms of lubricant in any one of the following manners (b)-(i) to (b)-(iv) and (c)-(v) for use as a liquid lubricant, semisolid lubricant or a dry film forming lubricant.

(b) Liquid lubricant, Semisolid lubricant (i) A small amount of liquid such as water, organic solvents (e.g., alcohols, glycols, ethers, esters, cellosolves, hydrocarbons, halogenated hydrocarbons, etc.), mineral oil, synthetic lube oil, and other oils is added to the melamine/(iso)cyanuric acid adduct to prepare a paste;

(ii) The melamine/(iso)cyanuric acid adduct is dispersed in any one of the liquids listed above, for use as a liquid lubricant;

(iii) The melamine/(iso)cyanuric acid adduct is blended into a viscous semisolid material such as a grease, fat and pitch, for use as a semisolid lubricant;

(iv) The adduct is used as a thickener which is incorporated in a base oil comprising mineral oil (of the type conventionally used as a lube oil) or synthesized lube oil, the resulting blend being used as grease;

(c) Dry film forming lubricant (v) The melamine/(iso)cyanuric acid adduct is incorporated in a film-forming resin composition such as aqueous polymer dispersion, a synthetic or natural resin paint, a thermosetting liquid resin paint, etc., applied to the surface to be lubricated, and dried to form a lubricating film.

In preparing lubricants in the manner described in (i) through (v) hereinabove, the melamine/(iso)cyanuric acid adduct may be effectively dispersed in an aqueous or oily medium or paint using a surfactant to treat the surface of the adduct prior to dispersion or by adding 0.01 to 10 parts by weight of a surfactant and/or dispersing agent to 100 parts by weight of the adduct in the course of mixing with the medium.

A melamine/(iso)cyanuric acid adduct prepared by dispersing melamine or (iso)cyanuric acid in an aqueous based solvent under stirring with the aid of a surfactant is economically used as an aqueous lubricant without any modification.

The melamine/(iso)cyanuric acid adduct of this invention can be incorporated in vehicles in varying amounts depending upon its application.

If the adduct is incorporated in water, alcohols, glycols, mineral oils or lube oils to form a free-flowing liquid lubricant, about 0.05 to 30 parts by weight and preferably about 0.5 to 10 parts by weight of the adduct is employed per 100 parts by weight of the liquid material. If the intended product is a paste lubricant, about 30 to 400 parts by weight and preferably about 50 to 300 parts by weight of the adduct is employed per 100 parts by weight of water, alcohols, glycols, mineral oils or lube oils.

If the adduct is added to a grease, the preferred amount of the adduct to be used ranges from about 0.1 to 100 parts by weight per 100 parts by weight of grease. Using less than about 0.1 part by weight of the adduct results in a lubricant which is low in the effect of increasing resistance to extremely high pressure, whereas using more than 100 parts by weight of the adduct provides too viscous a product which cannot effectively be used as a grease.

If a grease is prepared in the method of (b)-(iv), about 50 to 100 parts by weight and preferably about 10 to 30 parts by weight of the adduct are used per 100 parts by weight of a base oil such as a mineral oil or synthesized lube oil. Using less than 5 parts by weight of the adduct is not sufficient to provide a desired thickening effect whereas if the adduct is used in more than about 100 parts by weight it provides too viscous a product which cannot therefore be used as a grease. It is to be understood in this case that the melamine/(iso)cyanuric acid adduct may be used in combination with conventional thickeners for a grease, for instance, metallic soaps such as lithium soap, sodium soap, and calcium soap, or non-soap thickeners such as organic bentonite, polyurea, silica gel, and sodium terephthalamate.

Whether the melamine/(iso)cyanuric acid adduct of this invention is formulated into a liquid, grease or paste lubricant, about 0.01 to 10 parts by weight of a surfactant or dispersing agent added to 100 parts by weight of the adduct will render the adduct more stable in dispersion as well as increase its ability to provide higher resistance to extremely high pressures.

If the intended lubricant is a dry film which is mentioned in (c)-(v), about 10–400 parts by weight and preferably about 20–300 parts by weight of the adduct are used per 100 parts by weight of a film-forming resin.

The particle size of the adduct produced by the above-mentioned methods ranges from about 0.1 to 5 microns. For the lubricant use, regardless of the type of the lubricant, the particle size of the adduct is not critical within the above range. Smaller particle sizes of around 0.1 micron are preferred for the liquid type lubricant where better storage stability of the suspension is required.

4. Ingredients Other Than the Melamine/(Iso)cyanuric Acid Adduct (1) Mineral oils and synthetic lube oils Substantially any mineral oils that is currently used as a lube oil can be blended with the melamine/(iso)cyanuric acid adduct of this invention. For instance, paraffin base oils, naphthene base oils, and aromatic base oils, as classified by their physical properties; or spindle oil, precision machine oil, bearing oil, axle oil, compressor oil, gear oil, motor oil, gasoline engine oil, saturated cylinder oil, refrigerating oil, steam turbine oil, hydraulic turbine oil, insulating oil, quenching oil, annealing oil, antirusting oil, and air filter oil, as classified by their applications can be used.

Similarly about any synthetic lube oil can also be blended with the melamine/(iso)cyanuric acid adduct of this invention. For instance, diester oils such as sebacic diester and aliphatic diester; hydrocarbon oils such as ethylene polymerized oil and propylene polymerized oil; alkylated aromatics such as dodecyl benzene and didodecyl benzene; polyalkylene oxides such as polyethylene oxide and polypropylene oxide; polyglycidyl ether, polyvinyl ether, polyalkyl ether and esters thereof; halogenated hydrocarbons; amines and imines; acid amides; and silicone oil can be used. These mineral oils or synthetic lube oils may be used independently or as a mixture in proportions as desired.

Typical properties of the mineral oils or synthetic oils that can be used in the present invention are listed below:

| | Specific Gravity ($d^{20}$) | Viscosity Index |
|---|---|---|
| Paraffin base oils | 0.86–0.90 | 90–120 |
| Naphthene base oils | 0.90–0.95 | 30–80 |
| Aromatic base oils | 0.92–0.95 | 40–80 |
| Synthetic hydrocarbons | 0.84–0.90 | >105 |

(2) Grease

While there are no particular limitations on the type of grease that can be used in this invention, it is suitable to use grease which is composed of a base oil selected from the above illustrated mineral oils or synthetic lube oils plus a thickener selected from metallic soaps such as calcium soap, sodium soap, aluminum soap, lead soap, zinc soap, lithium soap, and mixed soap, or non-soap materials such as organic bentonite, polyurea, silica gel, sodium terephthalamate, etc. The consistency of the grease is generally in the range from 85 to 475 (penetration, mm/10, ASTM-217-66T), though the grease is not limited to those in this range.

(3) Aqueous dispersion medium

For its cheapness, water is the most preferred aqueous dispersion medium that can be used in this invention, but a mixture of water and water-soluble organic solvent may also be used. Examples of the water-soluble organic solvent that can be used in this invention are ethyl alcohol, ethylene glycol, propylene glycol, diethylene glycol, isopropyl alcohol, glycerin, polyethylene glycol, and a copolymer of ethylene oxide and propylene oxide.

(4) Surfactant and dispersing agent

The surfactant used for the production of the melamine/(iso)cyanuric acid adduct or incorporated in the lubricant can be freely selected from a wide variety of materials depending on the type of aqueous medium, lube oil and grease to which it is added. Examples of suitable surfactants are: anionic surfactants such as fatty acid soap, sodium higher alcohol sulfate, sodium alkylarylsulfonate, dialkyl sulfosuccinate, and condensate of sodium naphthalene sulfonate and formalin; cationic surfactants such as alkyl trimethyl ammonium chloride and alkyl pyridinium chloride; ampholytic surfactants such as sodium 1-hydroxyethyl-5-alkylimidazoline sulfate and alkyl betaine; nonionic surfactants such as polyoxyethylene alkyl phenyl ether, polyoxyethylene sorbitan alkyl ester, and a block polymer of ethylene oxide and propylene oxide; and nonionic-anionic surfactants such as sodium polyoxyethylene alkylaryl ether sulfonate.

These surfactants may be replaced by so-called dispersing agents such as carboxyethyl cellulose, hydroxyethyl cellulose, polyvinyl alcohol or a salt of polyacrylic acid. These surfactants or dispersing agents may be used singly or as a mixture and in amounts which depend on the object of application.

(5) Film-forming resin compositions

A desired type of paint that is to be combined with the melamine/(iso)cyanuric acid adduct can be selected depending upon the object of application, from a broad range of materials including liquid paints in aqueous or oily solvents and powder paints, so long as it can be finished into a dry film. Examples of suitable paints are: oily paints containing a drying oil, natural resin or the like as a base; synthetic resin paints based on an alkyd resin, butylated aminoalkyd resin, polyvinyl acetate, polyvinyl chloride, styrene-butadiene resin, acryl resin, epoxy resin, unsaturated polyester resin, phenolic resin, polyimide-polyisocyanate resin, silicone resin, and the like; synthetic resin emulsion paints based on polyvinyl acetate, polystyrene-butadiene, polyacrylic compound, and the like; and aqueous baking paints based on water-soluble phenol-aldehyde, etherified melamine resin, amine-neutralized alkyd resin, and the like.

The thickness for the film of dry lubricant is in the range of about 3 to 200 μm, preferably about 5 to 30 μm.

(6) Others

In preparing lubricants in the manner described in conjunction with 3 (b)-(i) to (c)-(v) above, the performance of the lube oil and grease may be improved by the addition of conventional additives such as oiliness improvers, extreme pressure additives, corrosion inhibitors, rust preventives, dispersing agents, pour point depressants, antifoaming agents, antioxidants, viscosity index improvers, flavor improvers and fluorescent dyes as set forth below.

Oiliness improvers: fatty acid, fatty acid soaps, higher alcohol esters, halogenated fatty acids and esters or amides thereof, halogenated fatty acid soaps, amine soaps of fatty acids, sulfonated oils of chlorinated fats, chlorinated and sulfur-treated products of animal and plant oils, etc.

Extreme pressure additives:

(a) Halogen-containing organic compounds such as halogenated hydrocarbons, halogenated fatty acids, halogenated fatty acid esters, phenols having chlorinated alkyl, chloronitrobenzoles, chloronitrophenols, polyvinyl chlorides, chlorinated terpene, chlorinated amines, etc.

(b) Sulfur-containing organic compounds such as disulfides, sulfur-treated products of fish and animal oils, olefins, polyisobutylenes, polystyrenes, unsaturated oils, sulfur-treated products such as terpene, oil and fat, chlorinated sulfur-treated product of oil and fat, and waxes, etc.

(c) Organophosphorus compounds such as triphenyl phosphite, tricresyl phosphate, triphenyl phosphine, triphenyl arsine, trialkyl phosphate, trialkyl phosphine, esters of diphosphoric acid, etc.

(d) Organonitrogenous compounds such as aromatic nitrile compounds, aminophenol derivatives of naphthenic acid, oleylcarbamade, etc.

Corrosion inhibitors: organosulfur compounds, organophosphorus compounds, amines, etc.

Rust preventives: oil and fat, fatty acid derivatives, organosulfur compounds, organophosphorus compounds, organonitrogenous compounds, etc.

Dispersing agents: petroleum sulfonates, anionic surfactants such as Turkey red oil, highly sulfonated oil or the like, sorbitan type nonionic surfactants, etc.

Pour point depressants: oil and fat, fatty acids, heavy metal soaps of fatty acids, glycols and derivatives thereof, octadecanol and condensate thereof, dimethylnaphthalene and derivatives thereof, wool fat, methacrylate polymers, condensates of chlorinated paraffins and naphthalene, condensates of higher olefins and naphthalene, condensates of chlorinated paraffins and phenolic acid, phthalates, bis(hydroxyalkyl)sulfide, etc.

Antifoaming agents: silicone oil.

Antioxidants: organic acids, amines, aminophenols, sulfur and selenium compounds, phosphorus compounds, organometallic compounds, etc.

Viscosity index improvers: methacrylate polymers, natural rubbers, synthetic rubbers, polyethylenes, polypropylenes, polyisobutylenes, copolymers of isobutylene and styrene, copolymers of fatty acids and vinyl esters, etc.

The selection of these additives and their use should be such that the melamine/(iso)cyanuric acid adduct of this invention is chemically stable in them.

5. Advantages of the Lubricant Prepared According to This Invention

A Solid lubricant consisting only of the melamine/(iso)cyanuric acid adduct of this invention is cheaper than the conventional solid lubricant, free from chemical toxicity and malodor, not corrosive on metals, and provides the intended lubricating performance under high loads. Compared with a conventional lube oil, grease and aqueous lubricant without the adduct, the solid lubricant of this invention provides high lubricating performance under high load, at high or low temperature, at low speed, under shock loading, under vacuum, and at high temperature and pressure.

In addition, a lube oil containing the adduct affords lower friction coefficient under high load than an adduct-free lube oil, and a load carrying capacity two to three times as high as the latter. This means the applicability of the adduct containing lube oil to shafts under extremely high loads, bearings, automotive gears, crankcases and other areas where the conventional lube oil cannot be effectively used because the lubricant film may rupture to have one metal surface directly contact the other. It also means that the lube oil containing the adduct will provide better results than the conventional lube oil in metal working, cutting and grinding of metals under extremely high pressure.

Further, the lubricant according to this invention which has the melamine/(iso)cyanuric acid adduct incorporated in the lube oil, grease or aqueous dispersion medium will have the following advantages over the one prepared by blending conventional molybdenum disulfide or colloidal graphite with lube oil or grease:

(i) Since the adduct is a white powder, the lubricant will not spoil the appearance of a machine or lubrication.

(ii) The adduct has a specific gravity close to that of a mineral oil and synthesized lube oil, and the particles of the adduct are fine, therefore, the adduct is stably dispersed in a lube oil, grease and an aqueous dispersion medium, with the result that settlement during storage can be easily prevented.

The adduct incorporated in a base oil to form grease functions as a thickener. Grease using the adduct as a thickener retains heat resistance, waterproofness, extended life at high temperature, and other features of grease using a conventional non-soap thickener; but as a further advantage, the adduct that also functions as a lubricant provides the grease with resistance to high load as well as to extremely high pressure.

The lubricant containing the melamine/(iso)cyanuric acid adduct of this invention can be formulated into the preparations defined in 3 (a) to (c) so that they assume a suitable form for application to specific purposes that include lubrication of contact surfaces of all kinds of rotary machines as well as machines having movable parts, lubrication for metal working such as cutting, grinding, rolling, quenching, annealing, pressing, drawing and rust prevention, lubrication of insulations having movable or sliding parts, lubrication of molds during plastics processing, prevention of seizure by coating the threads of bolts and nuts with the lubricant, and removal and disassembling of parts corroded to each other.

This invention will hereunder be described in greater detail by reference to the following examples which are given for illustrative purposes only and are by no means meant to limit the scope of this invention.

Preparation of the melamine/(iso)cyanuric acid adduct

A 5-liter stainless steel vessel was charged with an equimolar powder mixture of 200 g of melamine and 205 g of isocyanuric acid in 2 liters of water, the solution was then heated under stirring. The reaction temperature was elevated to 90° to 95° C. in about 30 minutes, upon which the production rate of a melamine/(iso)cyanuric acid adduct was accelerated and a viscous thixotropic slurry was formed. The reaction was brought to completion by holding the temperature at 90° C. for an additional 30 minutes. The resulting slurry having a high content of melamine/(iso)cyanuric acid adduct was filtered under vacuum to separate water, dried at 105° C. and ground to a powder of a high purity melamine/(iso)cyanuric acid adduct at a yield of substantially 100%. The adduct had a sublimation temperature of 440° C. Infrared absorption spectroscopy confirmed the absence of unreacted melamine and isocyanuric acid (see the Figure).

It is to be noted that isocyanuric acid is an isomer of cyanuric acid and that cyanuric acid of commercial grade is isocyanuric acid of the keto form.

EXAMPLE 1

A lubricant was prepared by mixing 70 parts by weight of commercial spindle oil #60 with 30 parts by weight of the melamine/(iso)cyanuric acid adduct (a particle size of 0.1 to 1$\mu$) prepared in the manner described above. A pendulum type oiliness friction tester manufactured by Shinko Zoki Co., Ltd. was used to measure the friction coefficient of the lubricant at 150° C. The result was a 30% decrease in the coefficient by comparison with the value for spindle oil #60.

EXAMPLE 2

A lubricant was prepared by mixing 1 kg of commercial spindle oil #60 with 300 g of the melamine/(iso)cyanuric acid adduct of this invention in a mortar.

A "Soda" 4-ball type lube oil tester (testing balls: $\frac{3}{4}$" steel ball for ball bearing, vertical shaft revolving at 200 rpm, product of Shinko Zoki) was used to measure the friction coefficient between balls under high load as well as the load carrying capacity. The results are shown in Table 1 below which also indicates the values for spindle oil #60 for comparison.

TABLE I

| Vertical Load | Friction Coefficient | |
|---|---|---|
| (kg) per Ball | Spindle Oil | Spindle Oil + Adduct |
| 50 | 0.105 | 0.091 |
| 60 | 0.110 | 0.090 |
| 70 | 0.111 | 0.085 |
| 80 | 0.107 | 0.083 |
| 90 | 0.103 | 0.080 |
| 100 | seizure | 0.082 |
| 120 | — | 0.092 |
| 140 | — | 0.083 |
| 160 | — | 0.091 |
| 180 | — | 0.104 |
| 185 | — | seizure |

Table 1 illustrates that as compared with the bare spindle oil, the melamine/(iso)cyanuric acid adduct and spindle oil combination affords a low friction coefficient between balls, thus exhibiting the intended lubricating performance under high load. Table 1 also shows a significant increase in the load carrying capacity, hence increased resistance to extremely high pressures.

EXAMPLE 3

A grease A was prepared by intimately mixing 70 parts by weight of a paraffin base mineral oil having kinematic viscosity of 105 cst at 37.8° C., viscosity index of 100 and specific gravity of 0.883 (15/4° C.) (Tellus Oil #41, a lube oil supplied by Shell Oil Co., U.S.A.) with 30 parts by weight of the melamine/(iso)cyanuric acid adduct in a mortar. A grease B was likewise prepared, except that the paraffin base mineral oil was replaced by Toshiba Silicone Oil TSF 451 (a lube oil supplied by Toshiba Electric Co.) as a base oil. Each grease sample was injected into Bearing #6309ZZ (a single row deep groove ball bearing manufactured by Nihon Seiko), which was then set on a motor driver shaft that remolved at 1450 rpm at room temperature. The motor was run for a period of 4 months, at the end of which the lubricating performance of the grease samples was observed. The results are shown in Table 2 below.

TABLE 2

| | Grease A<br>Paraffin Base | Grease B<br>Toshiba Silicone |
|---|---|---|
| Base Oil Used | Mineral Oil | Oil TSF 451 |
| Grease | | |
| Properties of | | |
| Grease | | |
| Appearance | white grease | white grease |
| Consistency | 356 | 348 |
| Dropping Point | 200° C. or higher | 200° C. or higher |
| Bearing Temp. | | |
| during Motor | room temp. + 22° C. | room temp. + 21° C. |
| Running | | |
| Test Results | | |
| State of Bearing | no damage or any | no damage or any |
| 4 Months Later | other defect | other defect |
| Properties of | | |
| Grease 4 Months | | |
| Later | | |
| Appearance | white grease | white grease |
| Consistency | 351 | 344 |
| Dropping Point | 200° C. or higher | 200° C. or higher |
| Other Remarks | no oil separation | no oil separation |

The above table shows that grease Samples A and B containing the melamine/(iso)cyanuric acid adduct as a thickener was white colored and that they could be used in extended service without affecting the ball bearing in any adverse way and without suffering any substantial change in properties.

EXAMPLE 4

A device comprising a metal disc having a cylindrical depression 5.1 mm across which engaged a rotating metal rod 5.0 mm across, with a thrust load of 1,000 g applied to its top, as well as a device of the same construction except that a small amount of the melamine/(iso)cyanuric acid adduct having a particle size of 0.3 to 1 micron was applied between the contact surfaces of the depression and rod were used to check the state in which the rods were revolved at 500 rpm at room temperature for 10 minutes as well as the state of the contact surfaces at completion of the rotation. The results of checking are set forth in Table 3 below.

TABLE 3

| Adduct | Not Used | Used |
| --- | --- | --- |
| State of Revolution | Abnormal metallic sound produced | Revolved quietly |
| Appearance* | Worn black metal powder on contact surfaces | White lubricant film on contact surfaces, with no evidence of worn metal |
| Temperature* | 10° C. higher than room temperature | Room temperature |

*State of contact surfaces after revolution

EXAMPLE 5

A lubricant was prepared by mixing 10 parts by weight of Albania Grease 2 (the trade name of grease supplied by Shell Oil) with 10 parts of the melamine/(iso)cyanuric acid adduct in an agate mortar. A "Soda" 4-ball type lube oil tester (testing balls: ¾" steel balls for ball bearing, vertical shaft revolving at 200 rpm, a product of Shinko Zoki) was used to measure the friction coefficient between balls under high load as well as the seizure load. The results are shown in Table 4 below which also indicates the values for Albania Grease 2 for comparison sake.

TABLE 4

| Vertical Load (lbs) per Ball | Comparison Friction Coefficient Albania Grease 2 | Example Friction Coefficient Albania Grease 2 + Adduct |
| --- | --- | --- |
| 17 | 0.075 | 0.074 |
| 38 | 0.077 | 0.077 |
| 58 | 0.078 | 0.075 |
| 79 | 0.081 | 0.078 |
| 99 | 0.077 | 0.077 |
| 120 | seizure | 0.079 |
| 140 | | 0.080 |
| 161 | | 0.077 |
| 181 | | 0.073 |
| 202 | | 0.073 |
| 222 | | 0.079 |
| 243 | | 0.085 |
| 263 | | seizure |

Table 4 indicates that as compared with Albania Grease 2 alone, the melamine/(iso)cyanuric acid adduct and Albania Grease 2 combination affords small friction coefficient between balls under high load as well as significantly high load carrying capacity.

EXAMPLE 6

A bench roll (3 rolls in parallel, manufactured by Tester Sangyo Co., Ltd.) was used to prepare a homogeneous dispersion of 100 parts by weight of the melamine/(iso)cyanuric acid adduct in 100 parts by weight of boiled oil as a base oil. The resulting preparation was a thixotropic semisolid material. It was applied to the inside surface of the cylindrical depression 5.1 mm across in the metal disc on a testing device of the same type as used in Example 4 and heated until a film was formed. While engaging the depression, the metal rod 5.0 mm across was revolved at 800 rpm at room temperature for a period of 30 minutes. Table 5 below shows the state of revolution as well as the state of the contact surfaces at completion of the revolution, as compared with the control wherein no adduct was applied to the inside surface of the cylindrical depression.

TABLE 5

| | Example | Comparison |
| --- | --- | --- |
| Film of adduct | Formed | Not formed |
| State of revolution | Quiet revolution | (1) Abnormal metallic sound generated (2) Tachometer needle continuously oscillated |
| State of contact surfaces after revolution | White lubricant film on contact surfaces, with no evidence at all of worn metal | Worn black metal powder on contact surfaces |

EXAMPLE 7

A one-liter stainless steel vessel was charged with an equimolar powder misture of 22.1 g of melamine and 22.5 g of isocyanuric acid in 500 ml of water, the solution was then heated under stirring. The reaction temperature was elevated to 90° to 95° C. in about 30 minutes, and thereafter the temperature 90° C. was held for additional 30 minutes to bring the reaction to completion. The friction coefficient of the resulting slurry of melamine/(iso)cyanuric acid adduct was measured in accordance with ring compression testing method. The tester employed an autographic recording device, and the test ring was a hollow cylinder (9.55 mm ID × 19.10 mm OD × 6.35 mm high, made of pure aluminum) which was subjected to heat treatment at 500° C. for 3 hours. A small amount of the adduct rich slurry was applied to both ends of the cylinder, which was sandwiched between two SKD steel sheets, with compressive load applied from above to cause plastic deformation at a compression rate of 1 mm/min. The friction coefficient was calculated from the measured values of compressibility and change in ID of the ring. The results of measurement are shown in Table 6 below which also indicates the values for water and spindle oil used independently for comparison sake.

TABLE 6

| | Comparison | | Example |
| --- | --- | --- | --- |
| | Water | Spindle Oil | Slurry of Adduct |
| Friction Coefficient | 0.30 | 0.07 | 0.055 |

Table 6 shows that the adduct of this invention affords friction coefficient which is significantly lower than water alone and is measurably lower than spindle oil.

While the invention has been described in detail and with reference to specific embodiments thereof, it will be apparent to one skilled in the art that various changes and modifications can be made therein without departing from the spirit and scope thereof.

What is claimed is:

1. A method for lubricating a surface which comprises applying an adduct of melamine and cyanuric acid or isocyanuric acid to a surface which is subject to wear.

2. The method of claim 1, wherein said adduct is applied as a solid.

3. The method of claim 1, wherein said adduct is applied dispersed in a liquid.

4. The method of claim 1, wherein said adduct is applied as a semisolid.

5. The method of claim 1, wherein said adduct is applied in a dry film.

6. The method of claim 3, wherein said liquid contains water.

7. The method of claim 3, wherein said liquid contains a mineral oil.

8. The method of claim 3, wherein said liquid contains a synthetic oil.

9. The method of claims 3 or 6, wherein said liquid contains an organic solvent.

10. The method of claim 3, wherein said adduct is present in said liquid in an amount of about 0.05 to 30 parts by weight per 100 parts by weight of said liquid.

11. The method of claim 4, wherein said semisolid is a grease.

12. The method of claim 4, wherein said semisolid is a fat.

13. The method of claim 4, wherein said semisolid is pitch.

14. The method of claim 11, wherein said grease is composed of a mineral oil or a synthetic oil as a base oil.

15. The method of claim 11, wherein said adduct is present in an amount of about 0.1 to 100 parts by weight per 100 parts of grease.

16. The method of claim 5, wherein said adduct is dispersed in a film-forming resin composition.

17. The method of claim 16, wherein said film-forming resin composition is an aqueous based composition or an oil based composition.

18. The method of claim 3, wherein said adduct is dispersed in said liquid as a paste.

19. The method of claim 18, wherein said liquid contains water.

20. The method of claims 18 or 19, wherein said adduct is present in an amount of about 30 to about 400 parts by weight per 100 parts by weight of said liquid.

21. The method of claims 3 or 4, wherein a surfactant or dispersing agent is additionally present.

22. A lubricant containing an adduct of melamine and isocyanuric acid.

23. A lubricant containing an adduct of melamine and isocyanuric acid dispersed in a liquid.

24. A lubricant containing an adduct of melamine and cyanuric acid or isocyanuric acid as a semisolid.

25. A lubricant comprising a dry film containing an adduct of melamine and cyanuric acid or isocyanuric acid.

26. The lubricant of claim 23, wherein said liquid contains water.

27. The lubricant of claim 23, wherein said liquid is non-aqueous.

28. The lubricant of claim 27, wherein said liquid contains a mineral oil.

29. The lubricant of claim 27, wherein said liquid contains a synthetic oil.

30. The lubricant of claim 27, wherein said liquid contains an organic solvent.

31. The lubricant of claims 23 or 27, wherein said adduct is present in an amount of about 0.05 to 30 parts by weight per 100 parts by weight of said liquid.

32. The lubricant of claim 24, wherein said semisolid is a grease.

33. the lubricant of claim 24, wherein said semisolid is a fat.

34. The lubricant of claim 24, wherein said semisolid is pitch.

35. The lubricant of claim 32, wherein said grease is composed of a mineral oil or a synthetic oil as a base oil.

36. The lubricant of claim 32, wherein said adduct is present in an amount of about 0.1 to 100 parts by weight per 100 parts by weight of grease.

37. The lubricant of claim 25, wherein said dry film is a film of a film-forming resin composition.

38. The lubricant of claim 37, wherein said resin composition is an aqueous based or oil based composition.

39. The lubricant of claim 23, wherein said adduct is dispersed in a liquid as a paste.

40. The lubricant of claim 39, wherein said liquid is non-aqueous.

41. The lubricant of claim 39, wherein said liquid contains water.

42. The lubricant of claims 39 or 40, wherein said adduct is present in an amount of about 30 to 400 parts by weight per 100 parts by weight of said liquid.

43. The lubricant of claims 23 or 24, wherein said lubricant additionally contains a surfactant or a dispersing agent.

44. A lubricant comprising an adduct of melamine and isocyanuric acid prepared at a pH of about 2 to 6.5 or 7.5 to 10.

* * * * *